(12) United States Patent
Sato et al.

(10) Patent No.: US 9,909,988 B2
(45) Date of Patent: Mar. 6, 2018

(54) LIGHT INTENSITY DETECTOR AND DETECTION METHOD

(71) Applicant: Sharp Kabushiki Kaisha, Osaka (JP)

(72) Inventors: Takanobu Sato, Osaka (JP); Noboru Iwata, Osaka (JP); Tazuko Kitazawa, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 15/107,929

(22) PCT Filed: Oct. 27, 2014

(86) PCT No.: PCT/JP2014/078503
§ 371 (c)(1),
(2) Date: Jun. 24, 2016

(87) PCT Pub. No.: WO2015/104885
PCT Pub. Date: Jul. 16, 2015

(65) Prior Publication Data
US 2016/0313245 A1    Oct. 27, 2016

(30) Foreign Application Priority Data

Jan. 9, 2014  (JP) ................................. 2014-002391

(51) Int. Cl.
*G01N 21/55* (2014.01)
*G01N 21/27* (2006.01)
*G01N 21/77* (2006.01)

(52) U.S. Cl.
CPC .......... *G01N 21/55* (2013.01); *G01N 21/274* (2013.01); *G01N 21/7703* (2013.01);
(Continued)

(58) Field of Classification Search
CPC ................... G01N 21/55; G01N 2201/06113
(Continued)

(56) References Cited

U.S. PATENT DOCUMENTS 5,766,956 A    6/1998  Groger et al.
7,414,244 B2 * 8/2008  Minamiura .......... G01N 21/314
                                                              250/338.1
(Continued)

FOREIGN PATENT DOCUMENTS

JP    2003130791 A    5/2003
JP    2005237867 A    9/2005
(Continued)

OTHER PUBLICATIONS

International Search Report of PCT/JP2014/078503 dated Jan. 20, 2015.

*Primary Examiner* — Seung C Sohn
(74) *Attorney, Agent, or Firm* — ScienBiziP, P.C.

(57) ABSTRACT

The invention intends to accurately measure a concentration of an object. An optical sensor (1) includes a detection light source (10) that emits measuring light, a light detection unit (40) that detects light intensity of the measuring light, which has been changed due to a change in optical characteristics of an object detection member (20), and a reference light source (11) that emits reference light. Light intensity of the reference light is detected by the light detection unit (40) without being affected by the change in the optical characteristics of the object detection member. The two light sources are arranged under the same environment.

8 Claims, 10 Drawing Sheets

(52) U.S. Cl.
CPC ............... *G01N 2021/7783* (2013.01); *G01N 2201/061* (2013.01); *G01N 2201/062* (2013.01); *G01N 2201/06113* (2013.01)

(58) Field of Classification Search
USPC ........................................................ 250/565
See application file for complete search history.

(56) References Cited

U.S. PATENT DOCUMENTS

| | | |
|---|---|---|
| 2012/0040475 A1 | 2/2012 | Bruls et al. |
| 2012/0330568 A1* | 12/2012 | Izawa ............... G01N 21/0303 702/24 |
| 2013/0094025 A1 | 4/2013 | Nishida et al. |

FOREIGN PATENT DOCUMENTS

| | | |
|---|---|---|
| JP | 2006090914 A | 4/2006 |
| JP | 2010107402 A | 5/2010 |
| JP | 2012518169 A | 8/2012 |
| JP | 2013088244 A | 5/2013 |

* cited by examiner

LIGHT INTENSITY DETECTOR AND DETECTION METHOD

TECHNICAL FIELD

The present invention relates to a light intensity detector for detecting light intensity of measuring light that is used to measure a concentration of an object.

BACKGROUND ART

Optical sensors for sensing objects with the aid of light have been used so far in a variety of applications. Examples of those optical sensors are disclosed in Patent Literatures (PTLs) 1 and 2.

PTL 1 discloses a measurement method for use in a measuring device including a measuring chip and a reference chip, and utilizing attenuated total reflectance. In the disclosed measurement method, a sensitivity difference between the measuring chip and the reference chip is obtained with photodiodes (detection units) that are included respectively in the measuring chip and the reference chip. Then, an analyte is added to only the measuring chip, a measurement result of the reference chip is calibrated with the above-mentioned sensitivity difference, and a measurement result of the measuring chip is corrected with the calibrated measurement result. This method measures a concentration of the analyte (object) by evaluating a change in the attenuated total reflectance.

PTL 2 discloses a molecule detector including a light source that emits light of a predetermined wavelength, an optical element including a waveguide (core layer) of a photonic crystal structure having changeable optical characteristics, and a detection unit that detects adsorption of a specific molecule on the basis of a change in light emitted from the optical element. A concentration of the specific molecule (object) adsorbed on the waveguide is measured by the detection unit evaluating a change in the optical characteristics of the waveguide. Furthermore, in the disclosed molecule detector, when there are plural waveguides, the above-mentioned measurement can be performed free from influences of environmental changes, etc. by employing any one of the waveguides as a reference.

CITATION LIST

Patent Literature

PTL 1: Japanese Unexamined Patent Application Publication "No. 2003-130791 (Laid-open on May 8, 2003)"
PTL 2: Japanese Unexamined Patent Application Publication "No. 2006-90914 (Laid-open on Apr. 6, 2006)"

SUMMARY OF INVENTION

Technical Problem

In the inventions disclosed in PTLs 1 and 2, the light intensity of measuring light emitted from a light source is not changed depending on the concentration of the object. One or more components affected by the object are a metal film and a dielectric block, which are included in the measuring chip, in the invention of PTL 1, and the optical element in the invention of PTL 2.

Thus, in the inventions of PTLs 1 and 2, it is not purported to correct a result of measuring the intensity of light emitted from the light source that is affected by optical characteristics as described above, and to improve the accuracy in measuring the concentration of the object.

The present invention has been made in consideration of the above-described problem, and a purpose of the present invention is to realize a light intensity detector that can accurately measure a concentration of an object.

Solution to Problem

To solve the above-mentioned problem, a light intensity detector according to an embodiment of the present invention comprises:

an object detection member having optical characteristics that are changed depending on a concentration of an object;
a first light source that emits measuring light used to measure the concentration of the object;
a first light detection unit that detects light intensity of the measuring light, which has been changed due to a change in the optical characteristics of the object detection member;
a second light source that emits reference light used to correct the light intensity of the measuring light, which has been detected by the first light detection unit; and
a second light detection unit that detects light intensity of the reference light,
wherein the light intensity of the reference light emitted from the second light source is detected by the second light detection unit without being affected by the change in the optical characteristics of the object detection member, and
the first light source and the second light source are arranged under same environment.

Furthermore, to solve the above-mentioned problem, a detection method according to an embodiment of the present invention comprises:

a measuring light emitting step of emitting, from a first light source, measuring light used to measure a concentration of an object;
a measuring light detecting step of detecting, by a first light detection unit, light intensity of the measuring light that has been applied to an object detection member having optical characteristics changeable depending on the concentration of the object, the light intensity of the measuring light being changed due to a change in the optical characteristics of the object detection member;
a reference light emitting step of, from a second light source arranged under same environment as that of the first light source, emitting reference light used to correct the light intensity of the measuring light, which has been detected by the first light detection unit; and
a reference light detecting step of detecting, by a second light detection unit, light intensity of the reference light without being affected by the change in the optical characteristics of the object detection member.

Advantageous Effects of Invention

According to the embodiments of the present invention, the concentration of the object can be accurately measured by correcting the light intensity of the measuring light with the use of the light intensity of the reference light.

BRIEF DESCRIPTION OF DRAWINGS

FIG. 3(a) is a schematic sectional view illustrating the practical configuration of the detection light source, and FIG. 3(b) is a schematic sectional view illustrating the practical configuration of the reference light source.

DESCRIPTION OF EMBODIMENTS

Embodiment 1

An embodiment of the present invention will be described in detail below with reference to FIGS. 1 to 5.

<Configuration of Optical Sensor>

Figure 1:
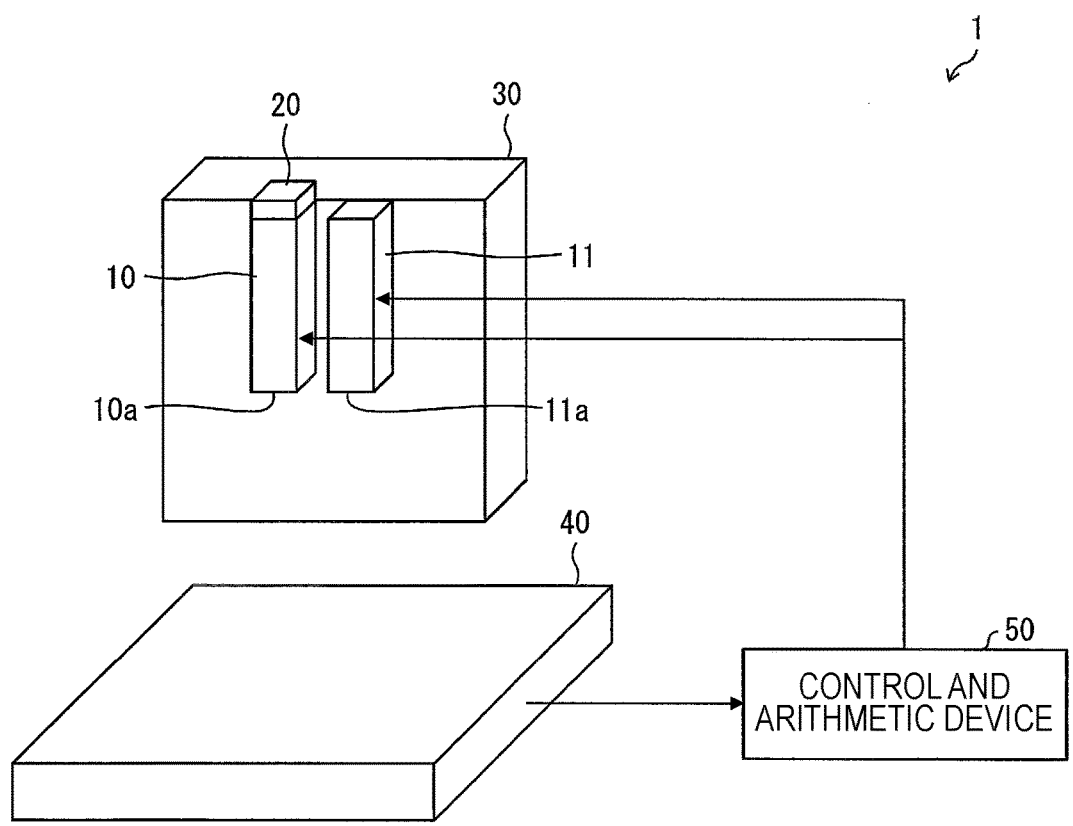
FIG. 1 is a schematic view illustrating a basic configuration of an optical sensor according to one embodiment of the present invention.
Figure 2:
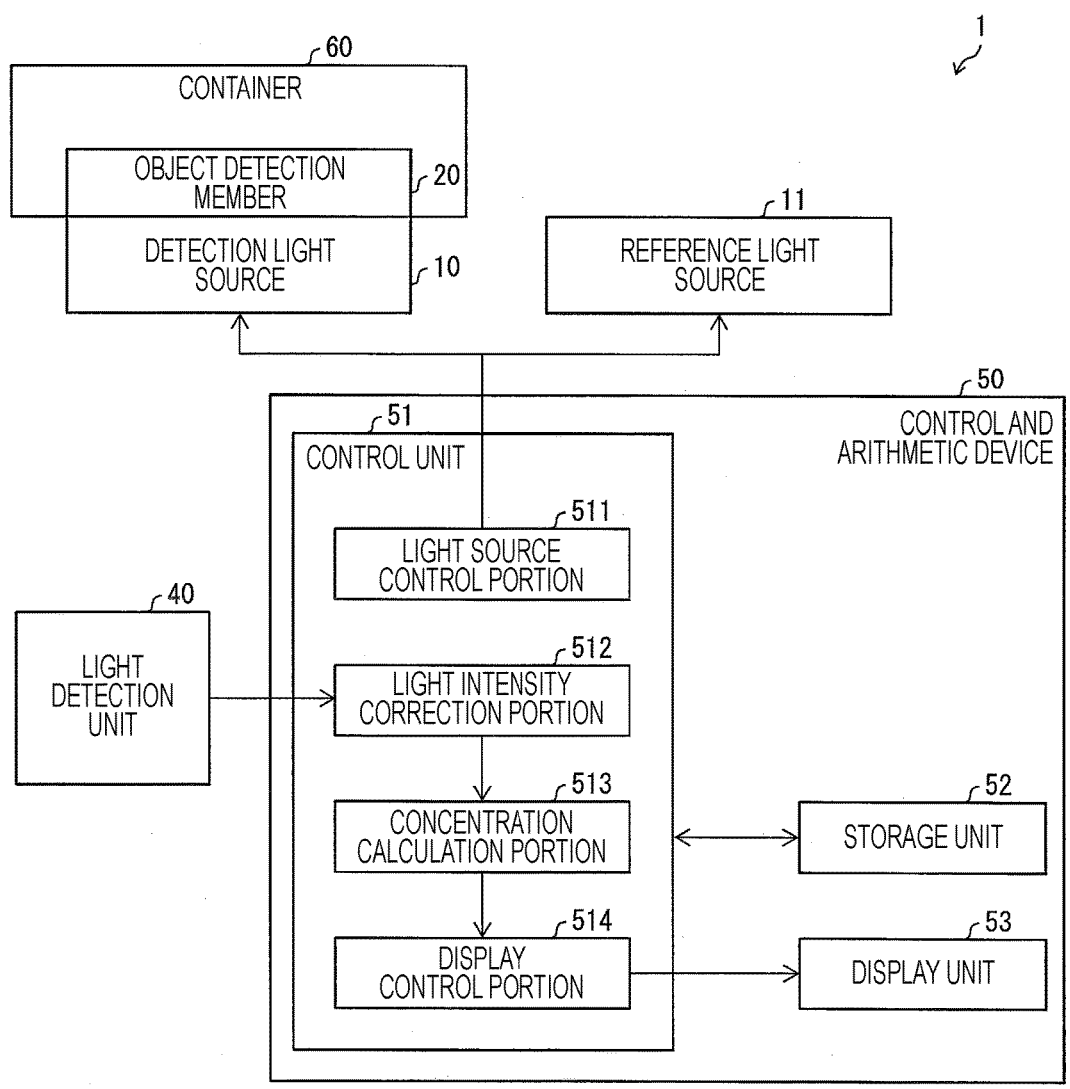
FIG. 2 is a block diagram illustrating the basic configuration of the optical sensor.

FIG. 1 is a schematic view illustrating a basic configuration of an optical sensor (light intensity detector) 1. FIG. 2 is a block diagram illustrating the basic configuration of the optical sensor 1. As illustrated in FIG. 1, the optical sensor 1 detects a change in optical characteristics of an object detection member 20, to which an object is supplied, as a change in light intensity. Furthermore, the optical sensor 1 measures a concentration of the object, i.e., the measurement object (detection object), (namely, evaluates the object) by evaluating the detected change in the light intensity. The optical sensor 1 mainly includes a detection light source (first light source) 10, a reference light source (second light source) 11, an object detection member 20, a support base 30, a light detection unit 40 (first detection unit and second detection unit), and a control and arithmetic device 50. A basic structure of the optical sensor 1 is constituted by the detection light source 10, the reference light source 11, the object detection member 20, and the light detection unit 40. The optical sensor 1 is just required to be able to detect at least the light intensity of measuring light that is emitted from the detection light source 10, and the light intensity of reference light that is emitted from the reference light source 11. As an exemplary modification, the control and arithmetic device 50 may be disposed in an apparatus separate from the optical sensor 1.

The detection light source 10 emits, to the light detection unit 40, the measuring light used to measure the concentration of the object. The detection light source 10 has an emission end 10a through which the measuring light is emitted, and the emission end 10a is arranged to face the light detection unit 40.

The reference light source 11 emits, to the light detection unit 40, the reference light used to correct the light intensity of the measuring light, which is obtained as a result of irradiating the light detection unit 40 with the measuring light emitted from the detection light source 10. In other words, the reference light source 11 emits the reference light used to correct the light intensity of the measuring light that is detected by the light detection unit 40. The reference light source 11 has an emission end 11a through which the reference light is emitted, and the emission end 11a is arranged to face the light detection unit 40.

Unlike the detection light source 10, the reference light source 11 does not emit light, which is affected by a change in the optical characteristics of the object detection member 20, to measure the concentration of the object. Hence the object detection member 20 is not arranged in the reference light source 11. Stated in another way, the reference light emitted from the reference light source 11 is detected by the light detection unit 40 without being affected by the change in the optical characteristics of the object detection member 20. Thus, the reference light source 11 can be said as being a light source different from the detection light source 10 that is affected by the change in the optical characteristics of the object detection member 20.

The reference light source 11 is arranged under substantially the same ambient environment as that of the detection light source 10. The detection light source 10 and the reference light source 11 are just required to be arranged under environments that are substantially the same in temperature, humidity, and atmosphere (e.g., atmospheric air), etc., and to be held in a positional relation enabling the light detection unit 40 to be irradiated with the respective lights emitted from both the light sources. Thus, because the reference light source 11 is arranged under substantially the same environment as that of the detection light source 10, a reaction of the reference light source 11 corresponding to a change in the ambient environment (i.e., a change in the light intensity of the reference light source 11 attributable to the change in the ambient environment) can be regarded as similar to a reaction of the detection light source 10. In FIG. 1, the reference light source 11 is arranged close to the detection light source 10 for easier realization of the above-mentioned arrangement.

The reference light source 11 and the detection light source 10 have substantially the same characteristics. In this embodiment, a light source being the same in type and model as the detection light source 10 is used as the reference light source 11. In particular, the reference light source 11 is preferably not only the same model as the detection light source 10, but also manufactured in the same lot as the detection light source 10. In other words, the reference light source 11 emits light on the basis of the same principle as the detection light source 10, and has substantially the same characteristics varying with time. As a result, just by controlling respective turned-on states of the detection light source 10 and the reference light source 11, the light intensity of the measuring light and the light intensity of the reference light can be detected under condition that an influence of change in the ambient environment is suppressed (preferably, the influence is eliminated). Here, the term "characteristics varying with time" implies a change in output of the emitted light with time when setting conditions, such as an output value, are held in a constant state.

The detection light source 10 and the reference light source 11 are elements that generate the measuring light and the reference light, respectively, upon application of currents applied to the light sources under control of the control and arithmetic device 50. For example, a semiconductor laser or a light emitting diode can be used as each of the detection light source 10 and the reference light source 11. In the case of using the semiconductor laser, the measuring light or the reference light having high output intensity can be emitted. The high output intensity makes it possible to increase a light quantity (signal) detected by the light detection unit 40, and to improve an SN ratio (Signal to Noise rate).

In addition, the detection light source 10 emits, to the light detection unit 40, the measuring light having been affected by the change in the optical characteristics of the object detection member 20 (i.e., the measuring light with the light intensity having been changed due to the change in the optical characteristics of the object detection member 20).

The object detection member 20 is a member to which or with which a sample containing an object is supplied or contacted. In FIG. 1, the object detection member 20 is arranged at an end of the detection light source 10 different from and opposite to the emission end 10a. It is to be noted that the detection light source 10 is just required to be able to emit the measuring light with the light intensity changed under the influence of the change in the optical characteristics of the object detection member 20 (i.e., depending on the change in the optical characteristics thereof). Thus, in another example, the object detection member 20 may be arranged in a part of a sidewall of the detection light source 10. The object and the sample may be each any of a solid, a liquid, and gas.

The object detection member 20 contains a material having optical characteristics that are changed depending on the concentration of the object upon receiving the light generated from the detection light source 10. In this embodiment, the object detection member 20 is formed by coating a film of the above-mentioned material on the opposite end of the detection light source 10.

Here, the term "optical characteristics" implies optical properties such as a refractive index (including a real part and an imaginary part), a transmittance, a reflectance, and an absorbance. When the object is redox gas, for example, one of various oxide semiconductors causing redox reactions with the redox gas and changing their optical characteristics can be used as the above-mentioned material. When a catalyst material is employed as the above-mentioned material, the optical characteristics of the object detection member 20 are temporarily changed by an intermediate that is generated when the catalyst material acts as a catalyst on the object. The presence of the object can be determined by detecting light intensity varied attributable to the above-described temporary change. When the object is an organic solvent, the above-mentioned material may be a polymer material that is expanded by absorbing the organic solvent, thereby changing its optical characteristics.

As illustrated in FIG. 1, the object detection member 20 to which the object is supplied is disposed in the detection light source 10, but it is not disposed in the reference light source 11. In other words, the object detection member 20 is arranged such that the measuring light detected by the light detection unit 40 is affected by the change in the optical characteristics of the object detection member 20, while the reference light detected by the light detection unit 40 is not affected by the change in the optical characteristics of the object detection member 20.

The support base 30 is a member for supporting the detection light source 10 and the reference light source 11. In FIG. 1, the detection light source 10 and the reference light source 11 are arranged on a flat surface of the support base 30 such that their emission ends 10a and 11a are positioned to face the light detection unit 40. In other words, the detection light source 10 and the reference light source 11 are arranged close to each other on the support base 30 that is in the form of a single base body (base plate). However, the detection light source 10 and the reference light source 11 are just required to be supported such that, as described above, they are arranged under substantially the same environment and are held in a positional relation enabling the light detection unit 40 to be irradiated with the respective lights emitted from both the light sources. Thus, it is not always required that the support base 30 has a shape having a flat surface, and that the detection light source 10 and the reference light source 11 are arranged on the single base body. The detection light source 10 and the reference light source 11 may be supported by a rod-shaped support member. As an alternative, the detection light source 10 and the reference light source 11 may be supported by separate support members.

A material of the support base 30 is, e.g., ceramic or resin. By employing such a material, heat generated from the detection light source 10 and the reference light source 11 can be dissipated. In other words, when the support base 30 is made of the above-mentioned material, the support base 30 can be caused to function as a heatsink. When the detection light source 10 and the reference light source 11 are semiconductor lasers, it is preferable in general that the support base 30 is made of ceramic. In such a case, the detection light source 10 and the reference light source 11 are bonded to the support base 30 by employing an Au—Sn solder.

The light detection unit 40 is an element that receives the measuring light emitted from the detection light source 10 and the reference light emitted from the reference light source 11, and that detects the light intensity of the measuring light and the light intensity of the reference light, respectively. For example, a photovoltaic element, such as a photodiode or a phototransistor, can be used as the light detection unit 40. The light detection unit 40 transmits optical signals representing the light intensity of the measuring light and the light intensity of the reference light, respectively, to the control and arithmetic device 50.

In the optical sensor 1, the light detection unit 40 is implemented with a single light detection unit for detecting the light intensity of the measuring light emitted from the detection light source 10 and the light intensity of the reference light emitted from the reference light source 11. Without being limited to the above-described case, the light intensity of the measuring light and the light intensity of the reference light may be detected by separate light detection units. Thus, it can be said that the light detection unit 40 in this embodiment has both functions of a first light detection unit 41 and a second light detection unit 42 in Embodiment 3.

The control and arithmetic device 50 measures the concentration of the object on the basis of the light intensity of the measuring light emitted from the detection light source 10. More specifically, in this embodiment, the control and arithmetic device 50 receives the above-mentioned optical signals, corrects the light intensity of the measuring light emitted from the detection light source 10 on the basis of the light intensity of the reference light emitted from the reference light source 11, and measures the concentration of the object on the basis of the corrected light intensity. Furthermore, the control and arithmetic device 50 performs lighting control of the detection light source 10 and the reference light source 11 (i.e., control of respective current amounts applied to both the light sources). A detailed configuration of the control and arithmetic device 50 will be described later.

The optical sensor 1 further includes a container 60 as illustrated in FIG. 2. The container 60 is a component capable of containing the sample, which contains the object, to supply the sample to the object detection member 20. In this embodiment, the container 60 is a closed-container having a supply port through which the sample is supplied to the inside of the container 60, and the object detection member 20 is partly fitted to be positioned inside the container 60 such that the sample is contacted with the object detection member 20. However, the container 60 is not limited to the above-mentioned structure insofar as the sample can be supplied to the object detection member 20. For example, a hole allowing the sample to be supplied to the object detection member 20 therethrough may formed in the container 60 (e.g., in a bottom portion of the container 60), and the hole may be positioned to face the object detection member 20. A container having an opened top instead of the supply port may also be used.

<Configuration of Control and Arithmetic Device>

The configuration of the control and arithmetic device 50 will be described below with reference to FIG. 2. The control and arithmetic device 50 includes a control unit 51, a storage unit 52, and a display unit 53.

The control unit 51 controls the control and arithmetic device 50 in its entirety. The control unit 51 includes a light source control portion 511, a light intensity correction portion 512, a concentration calculation portion 513, and a display control portion 514.

The light source control portion 511 performs the lighting control of each of the detection light source 10 and the reference light source 11. In this embodiment, the light source control portion 511 controls the detection light source 10 and the reference light source 11 to be turned on at different timings. Such control enables the light intensity of the measuring light and the light intensity of the reference light to be detected by the single light detection unit 40. A detailed control method will be described below.

The light intensity correction portion 512 receives the optical signals representing the light intensity of the measuring light and the light intensity of the reference light, respectively, from the light detection unit 40. Then, the light intensity correction portion 512 corrects the light intensity of the measuring light on the basis of the light intensity of the reference light. The light intensity correction portion 512 stores the corrected light intensity of the measuring light in the storage unit 52 and notifies the concentration calculation portion 513 of the fact that the corrected light intensity has been stored.

Upon receiving the notification from the light intensity correction portion 512, the concentration calculation portion 513 calculates the concentration of the object, which is contained in the object detection member 20, on the basis of the light intensity of the corrected measuring light. The concentration calculation portion 513 calculates the concentration of the object, for example, by referring to a graph representing the correlation between the light intensity of the measuring light and the concentration of the object, the graph being stored in the storage unit 52 in advance. When the concentration of the object is 0, the concentration calculation portion 513 may determine that the object is not present in the object detection member 20. The concentration calculation portion 513 stores the calculated concentration of the object, as a measurement result, in the storage unit 52 and notifies the display control portion 514 of the fact that the measurement result has been stored.

Upon receiving the notification from the concentration calculation portion 513, the display control portion 514 displays the measurement result on the display unit 53. At that time, a value of the light intensity of the corrected measuring light may be displayed as the measurement result.

The storage unit 52 stores various control programs to be executed by the control unit 51, the value of the light intensity of the measuring light corrected by the light intensity correction portion 512, the value of the concentration of the object, which has been calculated by the concentration calculation portion 513, and so on. The storage unit 52 is constituted by, e.g., a nonvolatile storage device such as a hard disk or a flash memory.

The display unit (presenting unit) 53 displays the values of the concentration of the object and the light intensity of the corrected measuring light, and so on, as the measurement results, under control of the display control portion 514. An example of the display unit 53 is a printer or a display.

<Practical Configurations of Detection Light Source and Reference Light Source>

Examples of practical configurations of the detection light source 10 and the reference light source 11 will be described below with reference to FIG. 3. FIG. 3(a) is a schematic sectional view illustrating the practical configuration of the detection light source 10, and FIG. 3(b) is a schematic sectional view illustrating the practical configuration of the reference light source 11.

In the optical sensor 1 according to this embodiment, a Fabry-Perot semiconductor laser (Fabry-Perot resonator) is used as each of the detection light source 10 and the reference light source 11. The Fabry-Perot semiconductor laser emits beams of laser light from both ends.

As illustrated in FIG. 3(a), the detection light source 10 includes a waveguide 13, a first mirror surface 14, and a second mirror surface 15. The waveguide 13 guides the generated laser light to each of the first mirror surface 14 and the second mirror surface 15, which are arranged at both the ends of the detection light source 10. When a current is applied (injected) to the waveguide 13, photons are generated inside the waveguide 13. The number of the generated photons increases in a chain-reaction way because the photons are repeatedly reflected by the first mirror surface 14 and the second mirror surface 15 to reciprocate inside the waveguide 13. As a result, light waves (i.e., laser light) formed by the photons come into a resonance state.

The first mirror surface 14 and the second mirror surface 15 are translucent to the laser light such that each mirror surface reflects the laser light while allowing the laser light having reached the resonance state to pass therethrough. Accordingly, first laser light 16 having reached the resonance state is emitted from the first mirror surface 14, and second laser light 17 having reached the resonance state is emitted from the second mirror surface 15.

The object detection member 20 is disposed in contact with the first mirror surface 14, and the light detection unit 40 is arranged to face the second mirror surface 15. For example, when the optical characteristics of the object detection member 20 are changed due to the presence of the object on the object detection member 20, optical characteristics of the first mirror surface 14 are also changed by an influence of the change in the optical characteristics of the object detection member 20. With the change in the optical characteristics of the first mirror surface 14, a reflectance of the first mirror surface 14 is changed. With the change in the reflectance, the resonance state (i.e., resonance conditions such as an oscillation threshold and differential efficiency) is also changed, whereby the light intensity of the second laser light 17 is changed. The light detection unit 40 detects a change in the light intensity corresponding to the change in the resonance state by detecting the light intensity of the second laser light 17 (i.e., the measuring light) that has passed through the second mirror surface 15. As a result, the control and arithmetic device 50 is able to measure the concentration of the object on the basis of the change in the light intensity of the measuring light, which has been affected by the change in the optical characteristics of the object detection member 20.

As described above, the Fabry-Perot semiconductor laser emits, to the light detection unit 40, the measuring light having the light intensity that has been changed due to the change in the optical characteristics of the object detection member 20. Thus, when the Fabry-Perot semiconductor laser is used as the detection light source 10, the light detection unit 40 detects the change in the light intensity of the measuring light, which has been caused due to the change in the above-described resonance conditions. A change amount of the light intensity resulting at that time is amplified by an optical gain effect that is developed within the Fabry-Perot resonator in the resonance state. Accordingly, sensitivity in detecting the light intensity of the measuring light can be improved in comparison with the case where the laser light is simply emitted to the object detection member 20 and a change in light intensity of reflected light resulting from reflection of the laser light by the object detection member 20 is detected.

Figure 3:
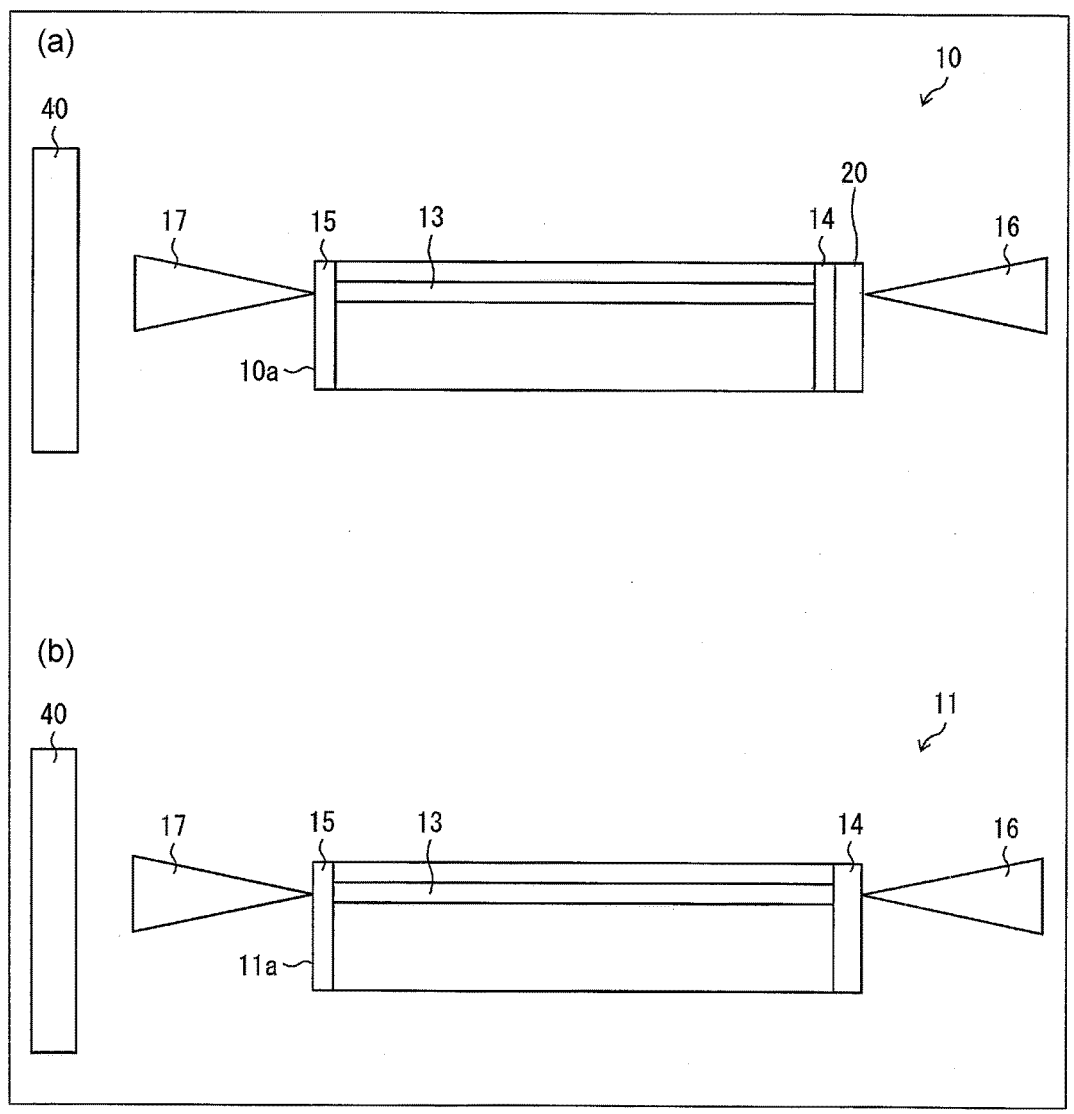
FIG. 3 illustrates examples of practical configurations of a detection light source and a reference light source, which are included in the optical sensor; more specifically.

On the other hand, as illustrated in FIG. 3(*b*), the reference light source 11 has a similar structure to that of the detection light source 10 except for a point that the object detection member 20 is not disposed. More specifically, in the reference light source 11, first and second laser lights 16 and 17 having reached the resonance state are emitted from first and second mirror surfaces 14 and 15, respectively. Because the reference light source 11 is not subjected to the above-mentioned change in the resonance state, which is caused by the influence of the object, unlike the detection light source 10, the reference light source 11 outputs the second laser light 17 (i.e., the reference light) having constant light intensity without being affected by factors other than changes in the ambient environment and deterioration over time.

<Operation of Optical Sensor>

Figure 4:
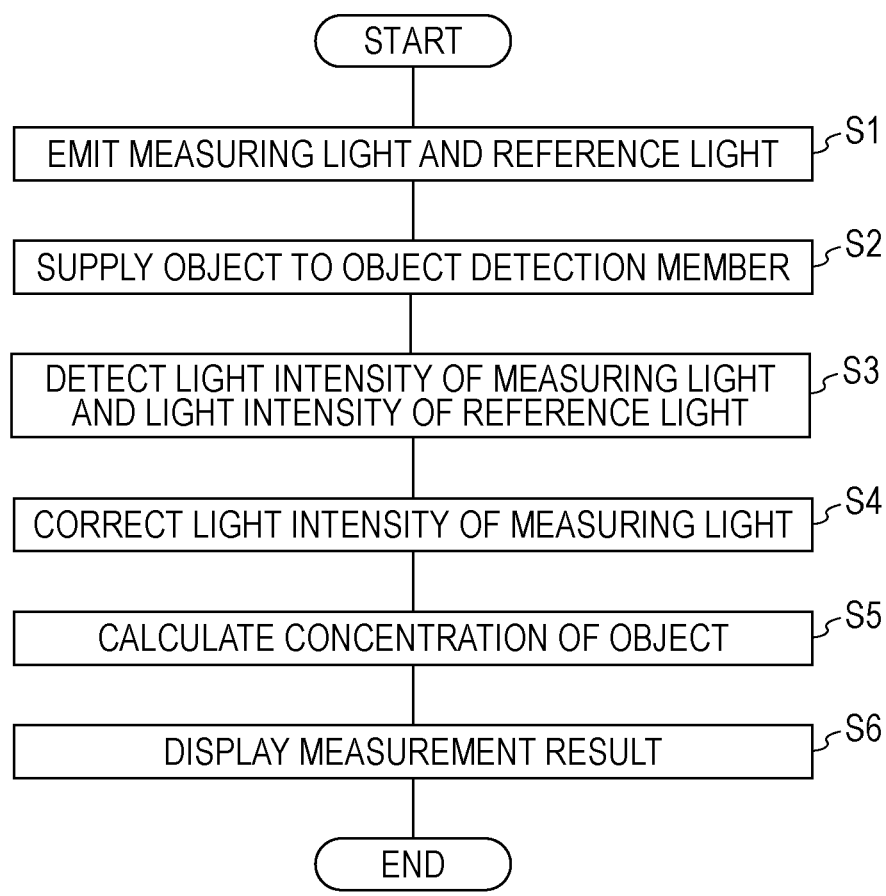
FIG. 4 is a flowchart illustrating an operation of the optical sensor.

FIG. 4 is a flowchart illustrating an operation of the optical sensor 1 (i.e., a detection method) according to this embodiment. Initially, as illustrated in FIG. 4, the optical sensor 1 is operated in a state where the object is not present in contact with the object detection member 20, turning-on of each of the detection light source 10 and the reference light source 11 is controlled by the light source control portion 511. The measuring light and the reference light are thereby emitted from the detection light source 10 and the reference light source 11, respectively (S1; measuring light emission step and reference light emission step). Then, the sample in the container 60 is supplied to the object detection member 20 such that the sample containing the object is contacted with the object detection member 20 in the optical sensor 1 (S2).

The processes of S1 and S2 may be executed in a sequence reversed to the above-described one, or may be executed at the same time. The supply of the sample to the object detection member 20 may be controlled, for example, by the control unit 51 that executes control of opening and closing the supply port of the container 60. As an alternative, the supply of the sample may be manually controlled.

Then, the light detection unit 40 detects the light intensity of the measuring light emitted from the detection light source 10 and the light intensity of the reference light emitted from the reference light source 11, and transmits optical signals representing the detected light intensities, respectively, to the light intensity correction portion 512 (S3: measuring light detection step and reference light detection step). The light intensity correction portion 512 analyzes those optical signals, corrects the light intensity of the measuring light on the basis of the light intensity of the reference light, and stores the corrected light intensity of the measuring light in the storage unit 52 (S4).

Here, the light intensity of the measuring light is changed attributable to not only the concentration of the object, but also the ambient environment of the detection light source 10, such as temperature. Therefore, with the process of detecting only the light intensity of the measuring light, the optical sensor 1 cannot determine whether the detected change in the light intensity is generated attributable to the object or due to a change in the ambient environment.

In consideration of the above point, the optical sensor 1 utilizes the light intensity of the reference light, which has been emitted from the reference light source 11 to the light detection unit 40, in order to obtain the light intensity of the measuring light for which the influence of the change in the ambient environment is suppressed. Because the reference light source 11 is not affected by the optical characteristics of the object detection member 20, the light intensity of the reference light emitted from the reference light source 11 is not changed attributable to the object. More specifically, in one example, the light intensity correction portion 512 subtracts the light intensity of the reference light, which is not affected by any change in the object detection member 20, from the light intensity of the measuring light. As a result, it is possible to eliminate the change in the light intensity of the measuring light, which is generated due to the change in the ambient environment, and to detect the change in the light intensity of the measuring light, which is generated attributable to the object. In other words, the influence of the ambient environment can be suppressed, and the light intensity of the measuring light corresponding to the concentration of the object (i.e., the corrected light intensity of the measuring light) can be obtained. Alternatively, the light intensity correction portion 512 may obtain, as a value of the corrected light intensity of the measuring light, a ratio of the light intensity of the measuring light to the light intensity of the reference light.

In the case of using the Fabry-Perot semiconductor laser, because the object detection member 20 is formed (as a film) on the first mirror surface 14 in the detection light source 10, the object detection member 20 cannot be removed from the detection light source 10. In that case, calibration work of removing the object detection member 20 and evaluating a state of the detection light source 10 in advance cannot be performed, and a change in an optical output caused by deterioration of the detection light source 10 cannot be corrected. Even with the constitution described above, however, by utilizing the reference light emitted from the reference light source 11, it is possible to correct the change in the light intensity of the measuring light, which is generated due to not only the change in the ambient environment of the detection light source 10, but also deterioration of the detection light source 10.

After the light intensity of the measuring light has been corrected by the light intensity correction portion 512, the concentration calculation portion 513 calculates the concentration of the object, which is contained in the object detection member 20, on the basis of the corrected light intensity of the measuring light (S4). Then, the display control portion 514 displays the concentration of the object, which has been calculated by the concentration calculation portion 513, as the measurement result on the display unit 53 (S6). Alternatively, the corrected light intensity of the measuring light may be displayed as the measurement result on the display unit 53.

While, in the above-described operation flow, the measuring light and the reference light are emitted in S1 and the light intensity of the measuring light and the light intensity of the reference light are detected in S3, the present invention is not limited to the above-described operation flow. The operation flow may be modified, for example, to proceed through steps of (1) supplying the object to the object detection member 20, (2) emitting the measuring light from the detection light source 10 and detecting the light intensity of the measuring light, and thereafter (3) emitting the reference light from the reference light source 11 and detecting the light intensity of the reference light. Alternatively, the above steps (2) and (3) may be executed in a reversed sequence, or the above three steps may be executed in the sequence of (3), (1) and (2).

<Lighting Control by Light Source Control Portion 511>

Figure 5:
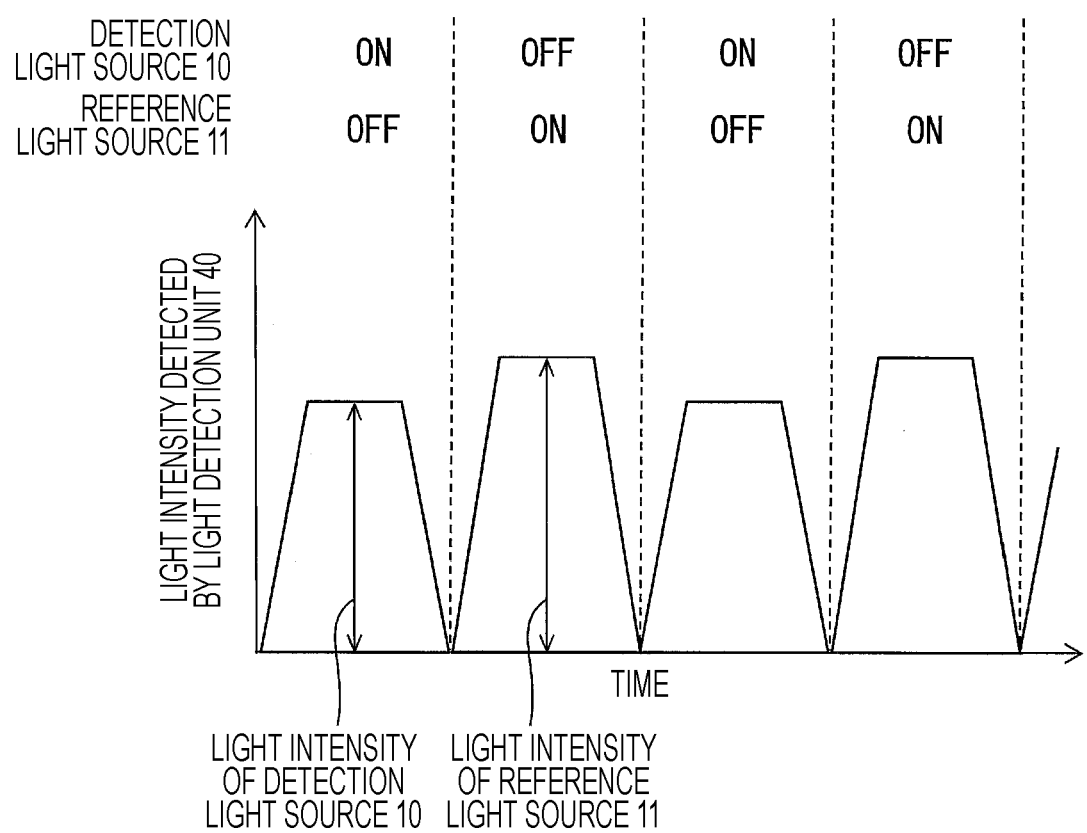
FIG. 5 is a timing chart illustrating one example of lighting control by a light source control unit that is included in the optical sensor.

The lighting control by the light source control portion 511 will be described below with reference to FIG. 5. FIG. 5 is a timing chart illustrating one example of the lighting control by the light source control portion 511.

In this embodiment, the light intensity of the measuring light and the light intensity of the reference light are detected by the single light detection unit 40. Therefore, when the measuring light and the reference light are emitted respectively from the detection light source 10 and the reference light source 11 at the same timing, the light detection unit 40 detects the light intensity of the measuring light and the light intensity of the reference light at the same timing, and hence detects a total value of both the light intensities. In the above case, there is a possibility that the light intensity correction portion 512 cannot determine the light intensity of the measuring light and the light intensity of the reference light in a discriminated manner. To avoid such a phenomenon, the light source control portion 511 executes the lighting control of the detection light source 10 and the reference light source 11, as illustrated in FIG. 5.

As illustrated in FIG. 5, in a first zone, the detection light source 10 is in a turned-on state, and the reference light source 11 is in a turned-off state. Thus, because the light applied to the light detection unit 40 in the first zone is the measuring light emitted from the detection light source 10, the light detection unit 40 detects the light intensity of the measuring light. On the other hand, in a next zone, the detection light source 10 is in a turned-off state, and the reference light source 11 is in a turned-on state. Thus, because the light applied to the light detection unit 40 in this zone is the reference light emitted from the reference light source 11, the light detection unit 40 detects the light intensity of the reference light. In addition, the light source control portion 511 notifies light source information indicative of the turned-on light source to the light intensity correction portion 512 in match with the above-mentioned timing of switching the turned-on state. As a result, the light intensity correction portion 512 can determine that the received optical signal represents the intensity of the light emitted from which one of the light sources.

With the above-described operation repeated under control of the light source control portion 511, respective changes in the light intensity of the measuring light and the light intensity of the reference light can be detected in real time independently of each other by the single light detection unit 40. By employing the above-described constitution, the optical sensor 1 can be provided at a relatively low cost because there is no need of installing the light detection unit 40 plural.

Preferably, the light source control portion 511 sets respective turned-on times of the detection light source 10 and the reference light source 11 in the successive zones equal to each other. In that case, since accumulated turned-on times of the detection light source 10 and the reference light source 11 are kept substantially equal to each other, the detection light source 10 and the reference light source 11 are deteriorated substantially at the same pace with the use of the optical sensor 1. Thus, time-dependent deteriorations of the detection light source 10 and the reference light source 11 can be held substantially in the same state by controlling the accumulated turned-on times to be kept substantially equal to each other with the light source control portion 511. Accordingly, the influence of the change in the light intensity of the measuring light, which is generated due to the deterioration of the detection light source 10, can be further suppressed by correcting the light intensity of the measuring light in the light intensity correction portion 512.

<Different Points Between Optical Sensor of This Embodiment and Related Art>

In the technique disclosed in PTL 1, the measuring chip and the reference chip have the same structure, and they are different just in whether a sample of a detection object contains an analyte (measuring chip) or the sample is only a solvent (reference chip). In the technique disclosed in PTL 2, a part of the waveguides included in the plural optical elements is used as a reference, and structures of the waveguides themselves are not different between the waveguide for measurement and the waveguide for reference.

Thus, the techniques disclosed in PTLs 1 and 2 do not have the features that the object detection member 20 having the optical characteristics changeable depending on the concentration of the object is disposed, and that the light intensity of the measuring light emitted from the detection light source 10 is detected by the light detection unit 40 after being affected by a change in the optical characteristics of the object detection member 20, while the light intensity of the reference light emitted from the reference light source 11 is detected by the light detection unit 40 without being affected by the change in the optical characteristics of the object detection member 20. In other words, in the disclosed techniques, the light intensity of the measuring light emitted from the light source is not changed depending on the concentration of the object. One or more components affected by the object are the metal film and the dielectric block, which are included in the measuring chip, in the invention of PTL 1, and the optical element in the invention of PTL 2.

Furthermore, unlike the above-described embodiment in which, for example, the semiconductor laser is used as the detection light source 10, a pair of light sources used in each of the techniques disclosed in PTLs 1 and 2 does not have such a difference as in the optical sensor 1 according to the above-described embodiment, i.e., the difference between the detection light source 10 emitting the measuring light that has been affected by the optical characteristics of the object detection member 20, and the reference light source 11 emitting the reference light that is not affected by the optical characteristics of the object detection member 20. Moreover, in the above embodiment, the detection light source 10 is affected by the change in the optical characteristics of the object, whereas the light sources are not affected by the object in the technique disclosed in PTLs 1 and 2.

In general, there occur an output variation attributable to a change in ambient environment of a light source (i.e., short-span output variation), and an output variation attributable to the element lifetime or deterioration of the light source (i.e., long-span output variation). In other words, the light source undergoes an output variation caused by external factors other than the influence of the change in the optical characteristics depending on the concentration of the object. Accordingly, various countermeasures are widely put into practice to suppress the above-mentioned output variation.

More specifically, one example of the countermeasure to the short-span output variation is addition of a device for keeping constant the ambient environment of the light source. When, for example, a semiconductor laser is used as the light source, it is required to add a temperature adjustment element, e.g., a Peltier element, to the optical sensor and to always adjust temperature by the temperature adjustment element in order to keep constant the temperature of the semiconductor laser. When a halogen lamp or a light emitting diode is used as the light source, a cooling and heating device, e.g., a heat dissipation fin or a fan, needs to be added to the optical sensor. In that case, the ambient environment of the light source is kept in a steady state by always operating the cooling and heating device to perform constant cooling and sufficient warming-up before starting detection of the light intensity of the measuring light.

However, when the temperature adjustment element or the cooling and heating device is added to the optical sensor, the following problems arise; (1) the size and the cost of the optical sensor are increased, (2) extra power is consumed to operate the above-mentioned element or device, and (3) when the warming-up is performed, the optical sensor cannot be operated during the warming-up.

One example of the countermeasure to the long-span output variation is to obtain a reference signal through calibration work before detecting the light intensity of the measuring light (i.e., before measuring the concentration of the object). An influence of the long-span output variation can be suppressed by correcting the light intensity of the measuring light with the reference signal being a reference. However, periodic calibration work is required, and the optical sensor cannot be used during the calibration work. In other words, problems arise in that the optical sensor cannot be made maintenance-free, and that real-time detection of the light intensity of the measuring light cannot be performed for a long period.

In this embodiment, as described above, the optical sensor 1 includes the object detection member 20 having the optical characteristics that are changed depending on the concentration of the object, the detection light source 10 for emitting the measuring light used to measure the concentration of the object, and the light detection unit 40 for detecting the light intensity of the measuring light, which has been changed due to a change in the optical characteristics of the object detection member 20. Stated in another way, the optical sensor 1 includes the detection light source 10 for generating the measuring light used to measure the concentration of the object, the object detection member 20 having the optical characteristics that are changed depending on the concentration of the object, thereby affecting the light intensity of the measuring light emitted from the detection light source 10, and the light detection unit 40 for detecting the light intensity of the measuring light, which has been changed due to a change in the optical characteristics of the object detection member 20. Furthermore, the reference light source 11 is disposed under the same environment as that of the detection light source 10, and the light intensity of the measuring light is corrected by employing the reference light that is emitted from the reference light source 11, and that is not affected by the change in the optical characteristics of the object detection member 20. In this embodiment, therefore, the light intensity of the measuring light can be corrected and the concentration of the object can be accurately measured without necessity of the various countermeasures to suppress the short-span output variation and the long-span output variation (such as the addition of the device for keeping constant the ambient environment of the light source and the acquisition of the reference signal before detecting the light intensity of the measuring light).

Embodiment 2

Another embodiment of the present invention will be described below with reference to FIG. 6. It is to be noted that, for convenience of explanation, components having the same functions as those of the components described in the above embodiment are denoted by the same reference sings and descriptions of those components are omitted.

Figure 6:
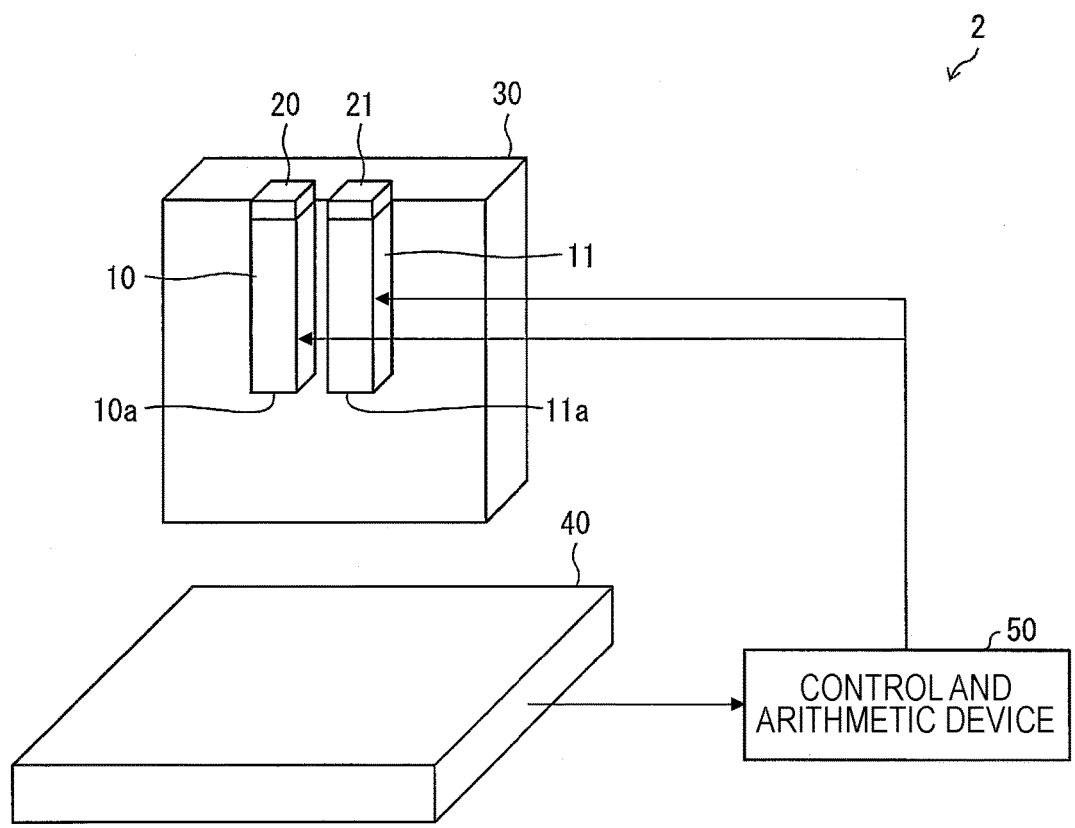
FIG. 6 is a schematic view illustrating a basic configuration of an optical sensor according to another embodiment of the present invention.

FIG. 6 is a schematic view illustrating a basic configuration of an optical sensor 2. As illustrated in FIG. 6, the optical sensor 2 includes the detection light source 10, the reference light source 11, the object detection member 20, a pseudo object detection member 21, the support base 30, the light detection unit 40, and the control and arithmetic device 50. This embodiment is different from Embodiment 1 in that the pseudo object detection member 21 is disposed in the reference light source 11.

The pseudo object detection member 21 is a member having substantially the same optical characteristics as those of the object detection member 20 under the environment where the object is not present. In other words, the pseudo object detection member 21 is a member having the optical characteristics that are not changed attributable to the object, or that are changed attributable to the object to a less extent in comparison with the object detection member 20. The pseudo object detection member 21 can be made of a material that is less susceptible to the influences of changes in the ambient environment, the influence attributable to supply of the object, etc., such as a chemically-stable oxide or nitride.

In FIG. 6, the pseudo object detection member 21 is arranged at an end of the reference light source 11 different from and opposite to its end positioned to face the light detection unit 40. The pseudo object detection member 21 may be arranged, for example, in a part of a sidewall of the reference light source 11 insofar as the reference light source 11 is able to emit the reference light that has been affected by the change in the optical characteristics of the pseudo object detection member 21.

Preferably, the pseudo object detection member 21 is arranged outside the container 60. In that case, because the object can be prevented from being supplied to the pseudo object detection member 21, the change in the optical characteristics of the pseudo object detection member 21, which is attributable to the presence of the object, can be suppressed reliably. Without being limited to the above-mentioned arrangement, a preventive member for preventing the supply of the object may be disposed to cover the surroundings of the pseudo object detection member 21.

The reference light source 11 emits, to the light detection unit 40, the reference light that is not affected by the change in the optical characteristics of the object detection member 20 as in Embodiment 1, but that is affected by the change in the optical characteristics of the pseudo object detection member 21.

Even under the environment where the object is not present in association with the object detection member 20, the optical characteristics of the object detection member 20 are changed due to the influences of the ambient environment, etc., and the light intensity of the measuring light outgoing from the object detection member 20 is also changed. In the optical sensor 2, because of including the pseudo object detection member 21, the reference light source 11 can emit, to the light detection unit 40, the reference light having the light intensity closer to the light intensity of the measuring light, which has been affected by the change in the optical characteristics of the object detection member 20 under the environment where the object is not present in association with the object detection member 20. Especially, when the detection light source 10 and the reference light source 11 are the Fabry-Perot semiconductor lasers as described above, respective resonance conditions of the detection light source 10 and the reference light source 11 can be made identical to each other under the environment where the object is not present in association with the object detection member 20. Thus, in the optical sensor 2, since the light intensity of the measuring light and the light intensity of the reference light under the environment where the object is not present in association with the object detection member 20 can be made closer to each other, the accuracy in correcting the light intensity of the measuring light can be further improved.

Embodiment 3

Still another embodiment of the present invention will be described below with reference to FIG. 7. It is to be noted that, for convenience of explanation, components having the same functions as those of the components described in the above embodiments are denoted by the same reference sings and descriptions of those components are omitted.

Figure 7:
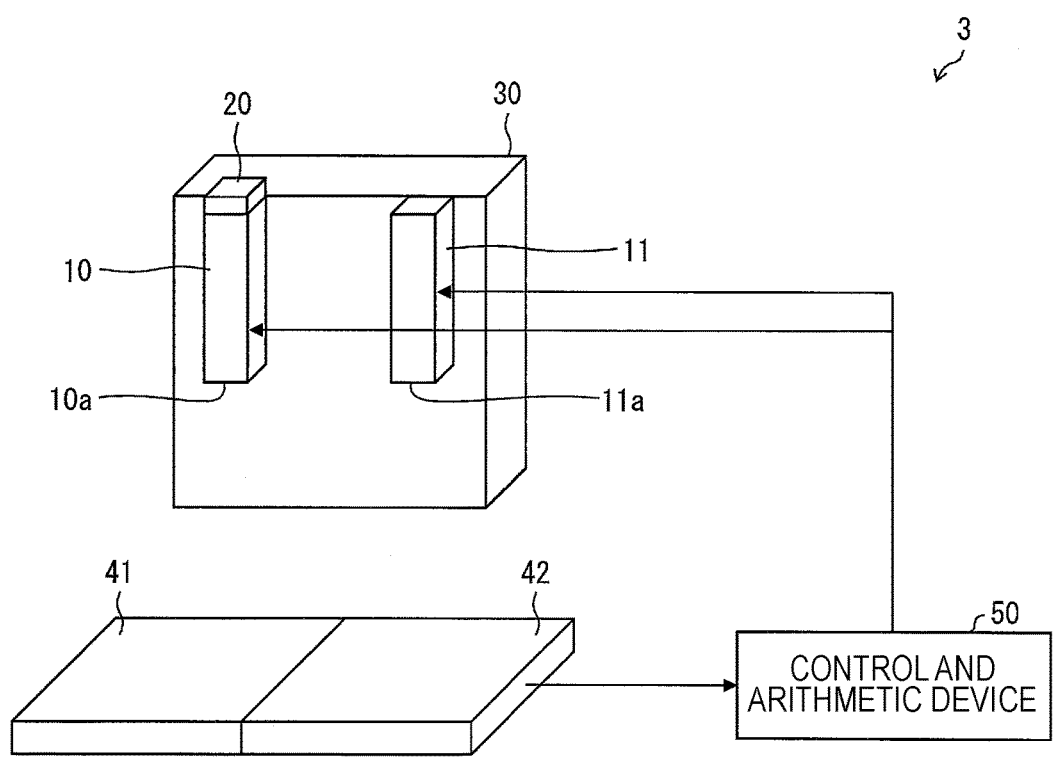
FIG. 7 is a schematic view illustrating a basic configuration of an optical sensor according to still another embodiment of the present invention.

FIG. 7 is a schematic view illustrating a basic configuration of an optical sensor 3 according to this embodiment. As illustrated in FIG. 7, the optical sensor 3 includes the detection light source 10, the reference light source 11, the object detection member 20, the support base 30, a first light detection unit 41, a second light detection unit 42, and the control and arithmetic device 50. This embodiment is different from Embodiments 1 and 2 in including the first light detection unit 41 and the second light detection unit 42 instead of the light detection unit 40.

Thus, in Embodiments 1 and 2, the light intensity of the measuring light emitted from the detection light source 10 and the light intensity of the reference light emitted from the reference light source 11 are detected by the single light detection unit 40. On the other hand, in this embodiment, the light intensity of the measuring light and the light intensity of the reference light are detected by separate light detection units, respectively.

The first light detection unit 41 is an element for receiving the measuring light emitted from the detection light source 10, and detecting the light intensity of the measuring light. The first light detection unit 41 is arranged to face the emission end 10a of the detection light source 10, and it transmits an optical signal representing the detected light intensity of the measuring light to the control and arithmetic device 50. On the other hand, the second light detection unit 42 is an element for receiving the reference light emitted from the reference light source 11, and detecting the light intensity of the reference light. The second light detection unit 42 transmits an optical signal representing the detected light intensity of the reference light to the control and arithmetic device 50. The first light detection unit 41 is arranged to face the emission end 10a of the detection light source 10. As in the light detection unit 40, a photovoltaic element, such as a photodiode or a phototransistor, can be used as each of the first light detection unit 41 and the second light detection unit 42.

In the optical sensor 3, as described above, the light intensity of the measuring light and the light intensity of the reference light are detected by the separate light detection units, respectively. In this embodiment, therefore, even when the light source control portion 511 (see FIG. 2) controls the detection light source 10 and the reference light source 11 to be continuously turned on at all times, the light intensity of the measuring light and the light intensity of the reference light can be detected independently of each other. In other words, it is not required to control the detection light source 10 and the reference light source 11 to be turned on at different timings (i.e., in a way of pulsed lighting illustrated in FIG. 5), as in Embodiment 1, in order to detect the light intensity of the measuring light and the light intensity of the reference light. Accordingly, the lighting control of the light source control portion 511 can be simplified in comparison with the case of controlling the detection light source 10 and the reference light source 11 with the pulsed lighting. Furthermore, the light intensity of the measuring light and the light intensity of the reference light emitted to the first light detection unit 41 and the second light detection unit 42, respectively, can be increased in the case of always-on lighting in comparison with the case of the pulsed lighting. As a result, an SN ratio for each of the measuring light and the reference light can be improved.

In this embodiment, when the detection light source 10 and the reference light source 11 are not turned on at all times, the light source control portion 511 preferably executes the lighting control of the detection light source 10 and the reference light source 11 such that turn-on timings and turn-off timings of the detection light source 10 and the reference light source 11 coincide with each other. With such control, since respective accumulated turned-on times of the detection light source 10 and the reference light source 11 can be made substantially equal to each other, the detection light source 10 and the reference light source 11 are deteriorated substantially at the same pace with the use of the optical sensor 3. In other words, time-dependent deteriorations of the detection light source 10 and the reference light source 11 can be kept substantially in the same state by controlling the respective accumulated turned-on times to be substantially equal to each other. Thus, as in Embodiment 1, the influence of the change in the light intensity of the measuring light, which is generated due to the deterioration of the detection light source 10, can also be suppressed.

The lighting control to make the respective accumulated turned-on times substantially equal to each other is not limited to the above-described process, and the lighting control may be executed in a manner of alternately controlling the detection light source 10 and the reference light source 11 as illustrated in FIG. 5.

Embodiment 4

Still another embodiment of the present invention will be described below with reference to FIGS. 8 and 9. It is to be noted that, for convenience of explanation, components having the same functions as those of the components described in the above embodiments are denoted by the same reference sings and descriptions of those components are omitted.

Figure 8:
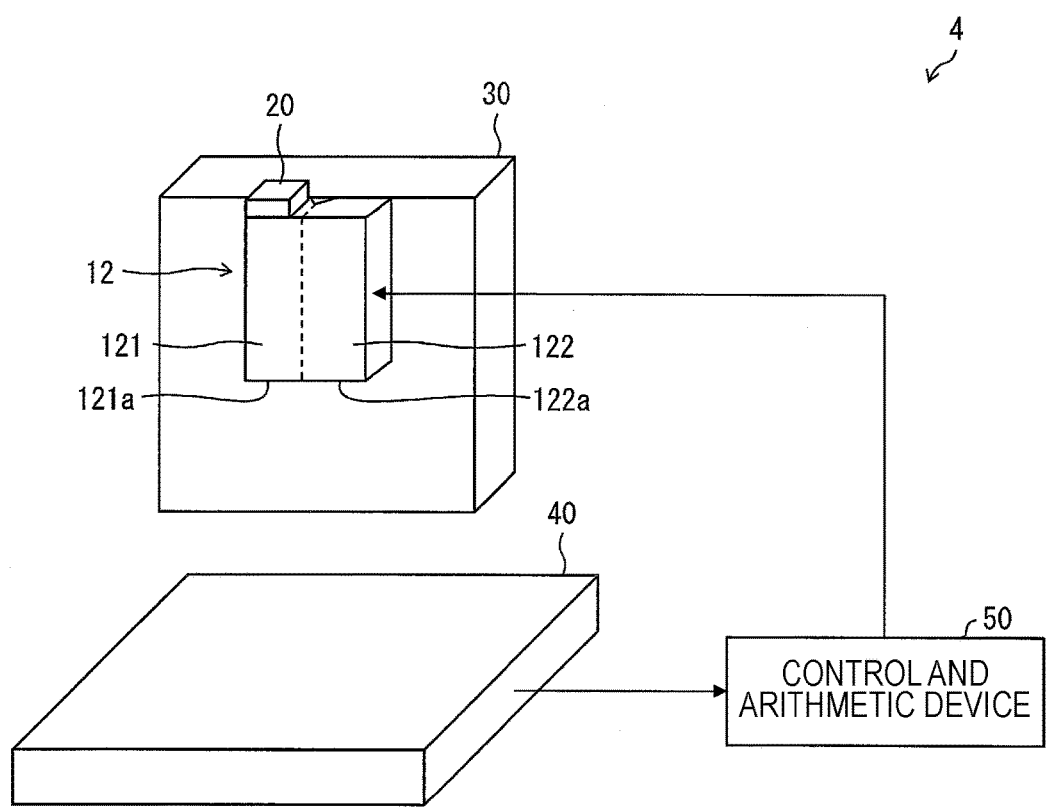
FIG. 8 is a schematic view illustrating a basic configuration of an optical sensor according to still another embodiment of the present invention.

FIG. 8 is a schematic view illustrating a basic configuration of an optical sensor 4 according to this embodiment. As illustrated in FIG. 8, the optical sensor 4 includes a monolithic semiconductor laser 12, the object detection member 20, the support base 30, the light detection unit 40, and the control and arithmetic device 50. This embodiment is different from Embodiments 1 to 3 in that the detection light source 10 and the reference light source 11 are not separate units and are implemented with a single semiconductor laser (i.e., the monolithic semiconductor laser 12) having the functions of those two light sources.

Figure 9:
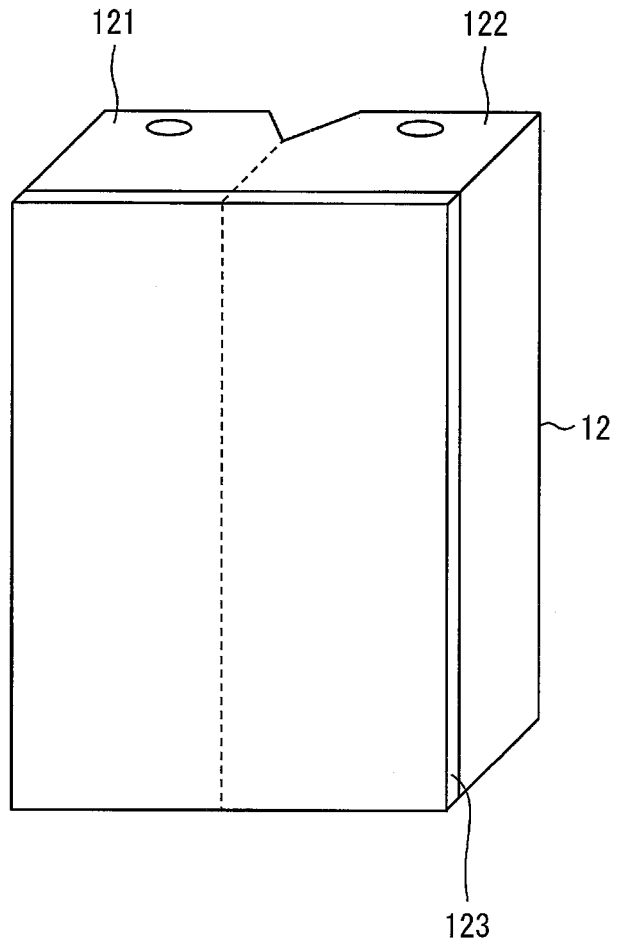
FIG. 9 is a schematic view illustrating a basic configuration of a monolithic semiconductor laser that is included in the optical sensor illustrated in FIG. 8.

FIG. 9 is a schematic view illustrating a basic configuration of the monolithic semiconductor laser 12. As illustrated in FIG. 9, the monolithic semiconductor laser 12 is constituted by forming (fabricating) a first semiconductor laser element 121 and a second semiconductor laser element 122 on a single chip 123. The monolithic semiconductor laser is generally used as a semiconductor laser in a device for recording and reproducing optical disks, for example.

The first semiconductor laser element 121 and the second semiconductor laser element 122 are constituted to be able to emit laser lights independently of each other, and they have emission ends 121a and 122a through which the laser lights are emitted, respectively, as illustrated in FIG. 8. Therefore, the first semiconductor laser element 121 and the second semiconductor laser element 122 function as independent light sources under control of the light source control portion 511 (see FIG. 2).

In this embodiment, the first semiconductor laser element 121 has the function of the detection light source 10, and the second semiconductor laser element 122 has the function of the reference light source 11. In that case, the emission end 121a serves as an end through which the measuring light is emitted, and the emission end 122a serves as an end through which the reference light is emitted. Without being limited to the above-described configurations, when the second semiconductor laser element 122 has the function of the detection light source 10, the first semiconductor laser element 121 functions as the reference light source 11.

As illustrated in FIG. 8, the first semiconductor laser element 121 and the second semiconductor laser element 122 are arranged such that the emission ends 121a and 122a are each positioned to face the light detection unit 40.

The object detection member 20 is disposed at an end of the first semiconductor laser element 121 functioning as the detection light source 10, the end being different from and opposite to the emission end 121a. When each of the first semiconductor laser element 121 and the second semiconductor laser element 122 has a structure similar to that of the Fabry-Perot semiconductor laser (see FIG. 3), the object detection member 20 is arranged to face the first mirror surface 14 present at the above-mentioned opposite end. On the other hand, the object detection member 20 is not disposed in association with the second semiconductor laser element 122 functioning as the reference light source 11.

Thus, also in this embodiment, the measuring light having been affected by the optical characteristics of the object detection member 20 is emitted from the first semiconductor laser element 121 functioning as the detection light source 10, as in Embodiment 1. On the other hand, the reference light having been not affected by the optical characteristics of the object detection member 20 is emitted from the second semiconductor laser element 122 functioning as the reference light source 11. Those emitted measuring light and reference light are detected by the light detection unit 40.

In the optical sensor 4, as described above, the detection light source 10 and the reference light source 11 are implemented with the monolithic semiconductor laser 12. More specifically, in the optical sensor 4, since the first semiconductor laser element 121 and the second semiconductor laser element 122 are arranged on the single chip 123, the ambient environment of the second semiconductor laser element 122 (i.e., the reference light source 11) can be made more closely identical to that of the first semiconductor laser element 121 (i.e., the detection light source 10). As a result, changes in the light intensity of the measuring light and the light intensity of the reference light attributable to a change in the ambient environment can be held substantially the same, whereby the influence of the ambient environment can be more reliably suppressed in the light intensity of the measuring light. Thus, the accuracy in correcting the light intensity of the measuring light can be further improved.

As in Embodiment 2, the pseudo object detection member 21 may be arranged at an end of the second semiconductor laser element 122 functioning as the reference light source 11, the end being different from and opposite to the emission end 122a.

Embodiment 5

Still another embodiment of the present invention will be described below. It is to be noted that, for convenience of explanation, components having the same functions as those of the components described in the above embodiments are denoted by the same reference sings and descriptions of those components are omitted.

In Embodiments 1 to 4, light sources of the same type and the same model are used as the detection light source 10 and the reference light source 11. This embodiment described below is concerned with the case of using light sources of different types or different models as the detection light source 10 and the reference light source 11. It is to be noted that the optical sensor in this embodiment may have any of the configurations of the optical sensors 1 to 4.

Here, the light sources of different types imply that light emission principles of those light sources are different from each other. In an exemplary case, a semiconductor laser is used as the detection light source 10, and a light emitting diode is used as the reference light source 11. Moreover, the light sources of different models imply that light emission principles of those light sources are the same, but their structures, materials, etc. are different from each other. In an exemplary case, semiconductor lasers emitting laser lights of different resonance wavelengths are used as the detection light source 10 and the reference light source 11. In this embodiment, for example, a 2-wavelength monolithic semiconductor laser (resonance wavelengths of laser lights: e.g., 660 nm and 780 nm) for CD and DVD can be used as a light source including the detection light source 10 and the reference light source 11 of different models. The 2-wavelength monolithic semiconductor laser is a light source that is mass-produced for use in devices of recording and reproducing optical disks, and that has succeeded in realization of cost reduction.

When the detection light source 10 and the reference light source 11 are different in type or model from each other, the light intensity of the measuring light and the light intensity of the reference light are changed in different ways corresponding to a change in the ambient environment. Thus, there is a possibility that the correction of eliminating the change in the light intensity of the measuring light, which is generated due to the change in the ambient environment, cannot be performed in the case of correcting the light intensity of the measuring light by simply employing the light intensity of the reference light.

To cope with such a possibility, in this embodiment, before the object is supplied to the object detection member 20, the light detection unit 40 previously detects respective changes in the light intensity of the measuring light and the light intensity of the reference light, which are generated due to the change in the ambient environment. The light intensity correction portion 512 (see FIG. 2) estimates the ambient environment of the detection light source 10 on the basis of the detected change in the light intensity of the reference light. More specifically, the light intensity correction portion 512 stores, in the storage unit 52, the change in the light intensity of the measuring light and the change in the light intensity of the reference light depending on the change in the ambient environment (e.g., temperature). Then, by referring to the storage unit 52, the light intensity correction portion 512 selects, as light intensity of the reference light (i.e., estimated light intensity of the reference light) to be used for the correction, the light intensity of the measuring light corresponding to the light intensity of the reference light that has been detected after the supply of the object to the object detection member 20. By employing the estimated light intensity of the reference light, the light intensity correction portion 512 corrects the light intensity of the measuring light that has been detected after the supply of the object to the object detection member 20.

As a result, even when the detection light source 10 and the reference light source 11 are different in type or model from each other, the influence of the ambient environment can be suppressed, and the light intensity of the measuring light can be corrected accurately.

Embodiment 6

Still another embodiment of the present invention will be described below with reference to FIG. 10. It is to be noted that, for convenience of explanation, components having the same functions as those of the components described in the above embodiments are denoted by the same reference sings and descriptions of those components are omitted.

Figure 10:
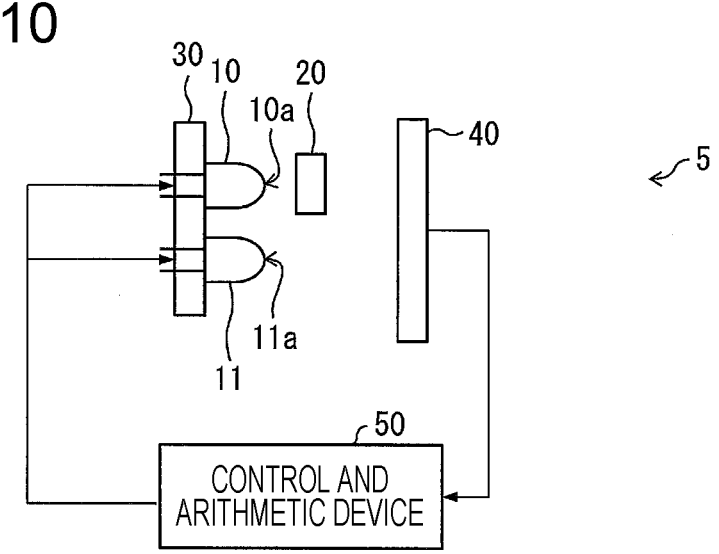
FIG. 10 is a schematic view illustrating a basic configuration of an optical sensor according to still another embodiment of the present invention.

FIG. 10 is a schematic view illustrating a basic configuration of an optical sensor 5. As illustrated in FIG. 10, the optical sensor 5 includes the detection light source 10, the reference light source 11, the object detection member 20, the support base 30, the light detection unit 40, and the control and arithmetic device 50. Embodiment 1 has been described above mainly in connection with the case of using the semiconductor lasers as the detection light source 10 and the reference light source 11. A practical configuration in the case of using light emitting dioses as the detection light source 10 and the reference light source 11 is described in this embodiment.

In this embodiment, the object detection member 20 is disposed (on an optical path of the measuring light) between the detection light source 10 and the light detection unit 40. The measuring light emitted from the detection light source 10 enters the object detection member 20, and the light intensity of the measuring light is changed under the influence of the change in the optical characteristics of the object detection member 20. The measuring light having the changed light intensity (i.e., the measuring light having passed through the object detection member 20) enters the light detection unit 40, and the light intensity of the measuring light is detected by the light detection unit 40. Stated in another way, the detection light source 10 is constituted so as to emit, to the light detection unit 40, the measuring light having the light intensity that has been affected by the change in the optical characteristics (transmittance) of the object detection member 20.

On the other hand, the object detection member 20 is not disposed (on an optical path of the reference light) between the reference light source 11 and the light detection unit 40. The reference light emitted from the reference light source 11 directly enters the light detection unit 40 without passing through the object detection member 20, and the light intensity of the reference light is detected by the light detection unit 40. Stated in another way, the reference light source 11 is constituted so as to emit, to the light detection unit 40, the reference light having the light intensity that has not been affected by the change in the optical characteristics (transmittance) of the object detection member 20.

Furthermore, the detection light source 10 and the reference light source 11 are supported on the support base 30 such that the emission end 10a of the detection light source 10 is positioned to face the object detection member 20 (i.e., the light detection unit 40), and that the emission end 11a of the reference light source 11 is positioned to face the light detection unit 40. In FIG. 10, the detection light source 10 and the reference light source 11 are arranged such that the sides opposite to the emission ends 10a and 11a (i.e., the substrate sides of the light emitting diodes) are positioned to face a flat surface of the support base 30. Without being limited to the above-described arrangement, however, the two light sources are just needed to be supported in a positional relation, as in Embodiment 1, that the detection light source 10 and the reference light source 11 are arranged under substantially the same environment to be able to emit the lights to the light detection unit 40.

In this embodiment, preferably, a base plate made of resin is used as the support base 30. In that case, the detection light source 10 and the reference light source 11 are bonded to the support base 30 by employing a general solder (e.g., a Sn—Pb solder)

With the configuration described above, even when the light emitting diodes are used as the detection light source 10 and the reference light source 11, the concentration of the object can be accurately measured by operating the optical sensor 5 in a similar manner to that in the optical sensor 1 in Embodiment 1, and by correcting the light intensity of the measuring light with the use of the light intensity of the reference light.

Embodiment 7

Still another embodiment of the present invention will be described below with reference to FIG. 11. It is to be noted that, for convenience of explanation, components having the same functions as those of the components described in the above embodiments are denoted by the same reference sings and descriptions of those components are omitted.

Figure 11:
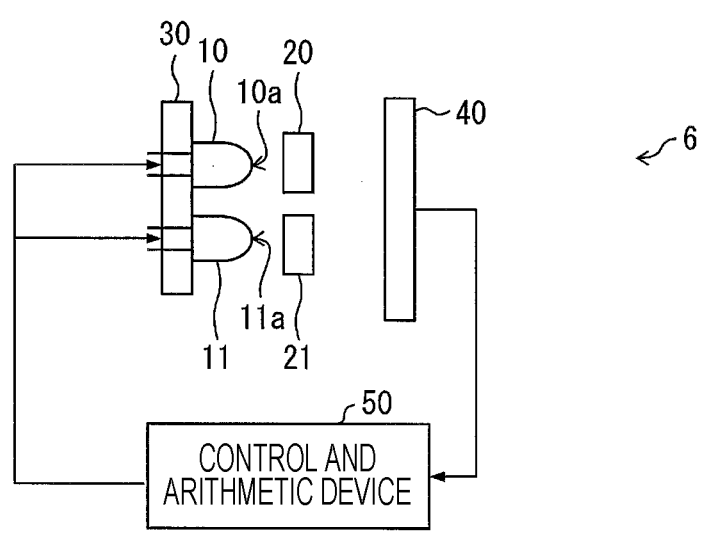
FIG. 11 is a schematic view illustrating a basic configuration of an optical sensor according to still another embodiment of the present invention.

FIG. 11 is a schematic view illustrating a basic configuration of an optical sensor 6. As illustrated in FIG. 11, the optical sensor 6 includes the detection light source 10, the reference light source 11, the object detection member 20, the pseudo object detection member 21, the support base 30, the light detection unit 40, and the control and arithmetic device 50. Embodiment 2 has been described above mainly in connection with the case of using the semiconductor lasers as the detection light source 10 and the reference light source 11. A practical configuration in the case of using light emitting dioses as the detection light source 10 and the reference light source 11 is described in this embodiment.

A positional relation among the detection light source 10, the object detection member 20, and the light detection unit 40 is the same as that in Embodiment 6. In the optical sensor 6, however, the pseudo object detection member 21 is arranged (on the optical path of the reference light) between the reference light source 11 and the light detection unit 40.

With the configuration described above, even when the light emitting diodes are used as the detection light source 10 and the reference light source 11, the accuracy in correcting the light intensity of the measuring light can be further improved in the optical sensor 6 because the light intensity of the measuring light and the light intensity of the reference light can be made closer to each other in the environment where the object is not present in association with the object detection member 20, as in the optical sensor 2 of Embodiment 2.

[Modifications]

In the case of using the semiconductor lasers as the detection light source 10 and the reference light source 11 like Embodiments 1 to 5, when the object contains a liquid, not only the object detection member 20, but also a top end surface (above-mentioned opposite end) of the reference light source 11 are needed to be contacted with the liquid. In FIG. 1, the top end surface of the reference light source 11 and a top end surface of the support base 30 are positioned substantially in the same plane. Therefore, when the top end surface of the reference light source 11 is contacted with the liquid in the object, the top end surface of the support base 30 is also contacted with the liquid. However, the top end surface of the support base 30 is not needed to be contacted with the liquid. In consideration of the above point, the top end surface of the reference light source 11 is preferably projected outward relative to the top end surface of the support base 30.

In the above case, the reference light source 11 may be arranged on the support base 30 such that the top end surface of the reference light source 11 is positioned in a plane including a top end surface of the object detection member 20 (i.e., a surface of the object detection member 20 on the side opposite to its surface facing the detection light source 10) in FIG. 1. The detection light source 10 may also be arranged on the support base 30 in a state projecting from the top end surface of the support base 30.

In the case of causing the support base 30 to function as a heatsink, when the detection light source 10 or the reference light source 11 is arranged in the state projecting from the top end surface of the support base 30, heat dissipation performance lowers correspondingly. Taking into account the above point, the detection light source 10 and the reference light source 11 are preferably arranged on the support base 30 such that the top end surface of the detection light source 10 and the top end surface of the reference light source 11 are positioned in the plane including the top end surface of the support base 30.

The light emitting diodes in Embodiments 5 and 6 may be used as the detection light source 10 and the reference light source 11 in Embodiment 3. In other words, the first light detection unit 41 and the second light detection unit 42 may be disposed to face the emission ends 10a and 11a of the detection light source 10 and the reference light source 11, respectively, which are each constituted by the light emitting diode.

[Implementation Example with Software]

Control blocks of the control and arithmetic device 50 (particularly, the light source control portion 511, the light intensity correction portion 512, the concentration calculation portion 513, and the display control portion 514 in the control unit 51) may be implemented with logical circuits (hardware) formed on an integrated circuit (IC chip), for example, or with software by employing a CPU (Central Processing Unit).

In the latter case, the control and arithmetic device 50 includes the CPU for executing commands of programs, i.e., software to implement various functions, a ROM (Read Only Memory) or a storage device (collectively called a "storage medium") in which the programs and various data are recorded in a state readable by a computer (or the CPU), a RAM (Random Access Memory) in which the programs are loaded, and so on. The purpose of the present invention is achieved by the computer (or the CPU) reading the programs from the recording medium and executing the programs. The recording medium used here may be a "non-temporary tangible medium", such as a tape, a disk, a card, a semiconductor memory, or a programmable logical circuit. Alternatively, the above-mentioned programs may be supplied to the computer via an arbitrary transmission medium (e.g., a communication network or broadcasting waves) capable of transmitting the programs. The present invention may also be implemented even in the case where the above-mentioned programs are in the form of data signals buried in carrier waves and are embodied through electronic transmission.

[Recapitulation]

A light intensity detector (each of the optical sensors 1 to 6) according to Aspect 1 of the present invention includes:

an object detection member (20) having optical characteristics that are changed depending on a concentration of an object;

a first light source (the detection light source 10) that emits measuring light used to measure the concentration of the object;

a first light detection unit (the light detection unit 40 or the first light detection unit 41) that detects light intensity of the measuring light, which has been changed due to a change in the optical characteristics of the object detection member;

a second light source (the reference light source 11) that emits reference light used to correct the light intensity of the measuring light, which has been detected by the first light detection unit; and a second light detection unit (the light detection unit 40 or the second light detection unit 42) that detects light intensity of the reference light, wherein the light intensity of the reference light emitted from the second light source is detected by the second light detection unit without being affected by the change in the optical characteristics of the object detection member, and the first light source and the second light source are arranged under same environment.

Furthermore, a detection method according to Aspect 8 of the present invention includes:

a measuring light emitting step (S1) of emitting, from a first light source (the detection light source 10), measuring light used to measure a concentration of an object;

a measuring light detecting step (S3) of detecting, by a first light detection unit (the light detection unit 40 or the first light detection unit 41), light intensity of the measuring light that has been applied to an object detection member having optical characteristics changeable depending on the concentration of the object, the light intensity of the measuring light being changed due to a change in the optical characteristics of the object detection member;

a reference light emitting step (S1) of emitting, from a second light source (the reference light source 11) arranged under the same environment as that of the first light source, reference light used to correct the light intensity of the measuring light, which has been detected by the first light detection unit; and a reference light detecting step (S3) of detecting, by the second light detection unit (the light detection unit 40 or the second light detection unit 42), light intensity of the reference light without being affected by the change in the optical characteristics of the object detection member.

With the features described above, the light intensity of the measuring light emitted from the first light source is changed due to a change in optical characteristics of the object detection member. The first light detection unit detects the light intensity of the measuring light, which has been changed due to the change in the optical characteristics of the object detection member. The concentration of the object can be measured by detecting the change in the light intensity of the measuring light in such a manner.

In general, the change in the light intensity of the measuring light occurs attributable to not only the change in the optical characteristics of the object detection member depending on the concentration of the object, but also change in the optical characteristics thereof due to a change in ambient environment. Accordingly, when the concentration of the object is measured from the light intensity of the measuring light detected by the first light detection unit, there is a possibility that an accurate value cannot be measured as the concentration of the object unless an influence of the change in the optical characteristics, which is caused by the change in the ambient environment, is suppressed.

According to one aspect of the present invention, the reference light used to correct the light intensity of the measuring light detected by the first light detection unit is emitted from the second light source, and the light intensity of the reference light is detected by the second light detection unit. Accordingly, the light intensity of the measuring light can be corrected by employing the light intensity of the reference light.

The light intensity of the reference light is not affected by the change in the optical characteristics of the object detection member. In addition, the first light source and the second light source are arranged under the same environment. Therefore, the light intensity of the reference light can be utilized as being the light intensity of the measuring light, which is obtained in the environment where the object is not present in association with the object detection member, and from which the influence of the change in the ambient environment is eliminated as far as possible. Thus, by correcting the light intensity of the measuring light with the use of the light intensity of the reference light, the influence of the change in the ambient environment can be suppressed, and the light intensity of the measuring light depending on the concentration of the object can be determined.

Hence the concentration of the object can be accurately measured by correcting the light intensity of the measuring light with the use of the light intensity of the reference light.

According to Aspect 2 of the present invention, in the light intensity detector according to Aspect 1, preferably, the first light source emits, as the measuring light, light having light intensity that is changed due to the change in the optical characteristics of the object detection member.

With the feature described above, the light intensity of the measuring light emitted from the first light source and having the light intensity, which has been changed due to the change in the optical characteristics of the object detection member, is detected by the first light detection unit. Even in that case, the concentration of the object can also be measured by correcting the light intensity of the measuring light with the use of the light intensity of the reference light.

According to Aspect 3 of the present invention, in the light intensity detector according to Aspect 1 or 2, preferably, the first light source and the second light source are light sources emitting lights on the basis of the same principle, and the first light source and the second light source are subjected to lighting control such that accumulated turned-on times of both the light sources are equal to each other.

With the features described above, deteriorations of the first light source and the second light source with the lapse of time can be kept substantially in the same state. It is hence possible to suppress a change in the light intensity of the measuring light, which is attributable to the deterioration of the first light source, and to accurately detect the light intensity of the measuring light depending on the concentration of the object.

According to Aspect 4 of the present invention, in the light intensity detector according to any one of Aspects 1 to 3, preferably, the second light source is arranged close to the first light source.

With the feature described above, the first light source and the second light source can be easily arranged under the same ambient environment.

According to Aspect 5 of the present invention, in the light intensity detector according to any one of Aspects 1 to 4, preferably, the first light source and the second light source are implemented with a monolithic semiconductor laser (12).

With the feature described above, the configuration in which the first light source and the second light source are arranged close to each other can be easily implemented. Thus, the first light source and the second light source can be positively arranged under the same environment.

According to Aspect 6 of the present invention, in the light intensity detector according to any one of Aspects 1 to 5, preferably, the first light detection unit and the second light detection unit are constituted as a single light detection unit (40), and the first light source and the second light source are subjected to lighting control at different timings.

Generally, in the case of turning on the first light source and the second light source at the same timing, because the single light detection unit detects the light intensity of the measuring light and the light intensity of the reference light at the same timing, it is impossible in the light intensity detector to determine whether the detected light intensity is the light intensity of the measuring light or the light intensity of the reference light. Hence the light intensity of the measuring light cannot be corrected by employing the light intensity of the reference light.

With the feature described above, since the first light source and the second light source are subjected to the lighting control at different timings, the above-mentioned problem can be avoided. Accordingly, the light intensity of the measuring light and the light intensity of the reference light can be detected independently of each other even with the single light detection unit. Furthermore, since there is no need of installing a plurality of light detection units, the optical sensor can be provided at a relatively low cost.

According to Aspect 7 of the present invention, in the light intensity detector according to any one of Aspects 1 to 6, preferably, the light intensity detector further includes a pseudo object detection member (21) having optical characteristics that are the same as the optical characteristics of the object detection member under environment in which the object is not present, and the light intensity emitted from the second light source is detected by the light detection unit after being affected by the optical characteristics of the pseudo object detection member.

With the features described above, the second light source emits the reference light having the light intensity affected by the optical characteristics of the pseudo object detection member, which are the same as the optical characteristics of the object detection member under the environment in which the object is not present. Therefore, the second light source can emit the reference light having the light intensity closer to that of the measuring light, which has been affected by a change in the optical characteristics of the object detection member under the environment in which the object is not present.

Thus, the light intensity detector can correct the light intensity of the measuring light by employing the light intensity of the reference light, and hence can improve the accuracy of the correction.

The light intensity detector according to each aspect of the present invention may be implemented with a computer. In that case, not only a light-intensity correction control program that is installed in the light intensity detector and that implements the light intensity detector with the computer by causing the computer to operate as various means in the light intensity detector, but also a computer-readable recording medium on which the relevant program is recorded fall within the scope of the present invention.

[Differently Expressions of Present Invention]

The present invention can be further expressed as follows.

(A) An optical sensor system (light intensity detector) according to one aspect of the present invention includes a detection light source, an object detection member, and a light detection unit, the optical sensor system detecting a detection object by measuring an optical signal that is input to the light detection unit from the detection light source, and that is changed depending on a change in optical characteristics of the object detection member, the change being generated attributable to the detection object, wherein the optical sensor system further includes a reference light source arranged close to the detection light source and placed under substantially the same ambient environment as that of the detection light source, and a measurement result of the optical signal input to the light detection unit from the detection light source is corrected on the basis of an optical signal input to the light detection unit from the reference light source that is affected by the change in the optical characteristics of the object detection member in a different way from the detection light source.

(B) According to one aspect of the present invention, in the optical sensor system stated in above (A), the detection light source and the reference light source may be light sources having substantially the same characteristic in time-dependent change, and accumulated turned-on times of both the light sources may be set equal to each other.

(C) According to one aspect of the present invention, in the optical sensor system stated in above (A) or (B), the detection light source and the reference light source may be semiconductor lasers and may be bonded to a single support base.

(D) According to one aspect of the present invention, in the optical sensor system stated in above (C), the detection light source and the reference light source may be a monolithic semiconductor laser fabricated on one chip.

(E) According to one aspect of the present invention, in the optical sensor system stated in any one of above (A) to (D), the detection light source and the reference light source may be turned on at different timings such that the optical signals of the detection light source and the reference light source can be evaluated by the single light detection unit independently of each other.

(F) According to one aspect of the present invention, in the optical sensor system stated in any one of above (A) to (E), the optical sensor system may further include a pseudo object detection member having optical characteristics that are substantially the same as the optical characteristics of the object detection member in environment where the detection object is not present, and that are less changed or not changed attributable to the detection object, and the optical characteristics of the pseudo object detection member may be reflected on the optical signal input from the reference light source.

(G) A detection method for use in the optical sensor system according to one aspect of the present invention detects a detection object by, with the use of a detection light source, an object detection member, and a light detection unit, measuring an optical signal that is input to the light detection unit from the detection light source, and that is changed depending on a change in optical characteristics of the object detection member, the change being generated attributable to the detection object, wherein the detection method corrects, by further employing a reference light source arranged close to the detection light source and placed under substantially the same ambient environment as that of the detection light source, a measurement result of the optical signal input to the light detection unit from the detection light source on the basis of an optical signal input to the light detection unit from the reference light source that is affected by the change in the optical characteristics of the object detection member in a different way from the detection light source.

The present invention is not limited to the above-described embodiments, and the present invention can be variously modified within the scope defined in Claims. Embodiments obtained by combining the technical means, disclosed in the different embodiments, with each other as appropriate also fall within the technical scope of the present invention. Moreover, novel technical features can be obtained by combining the technical means, disclosed in the embodiments, with each other.

INDUSTRIAL APPLICABILITY

The present invention can be utilized, for example, in measuring devices that measure concentrations of objects by utilizing light.

REFERENCE SIGNS LIST 1 optical sensor (light intensity detector)
2 optical sensor (light intensity detector)
3 optical sensor (light intensity detector)
4 optical sensor (light intensity detector)
5 optical sensor (light intensity detector)
6 optical sensor (light intensity detector)
10 detection light source (first light source)
11 reference light source (second light source)
12 monolithic semiconductor laser (first light source, second light source)
20 object detection member
21 pseudo object detection member
40 light detection unit (first light detection unit, second light detection unit)
41 first light detection unit
42 second light detection unit
121 first semiconductor laser element (first light source, second light source)
122 second semiconductor laser element (second light source, first light source)

What is claimed is:

1. A light intensity detector comprising:
an object detection member having optical characteristics that are changed depending on a concentration of an object;
a first light source that emits measuring light used to measure the concentration of the object;
a first light detection unit that detects light intensity of the measuring light, which has been changed due to a change in the optical characteristics of the object detection member;
a second light source that emits reference light used to correct the light intensity of the measuring light, which has been detected by the first light detection unit; and
a second light detection unit that detects light intensity of the reference light,
wherein the light intensity of the reference light emitted from the second light source is detected by the second light detection unit without being affected by the change in the optical characteristics of the object detection member, and
the first light source and the second light source are arranged under same environment.

2. The light intensity detector according to claim 1, wherein the first light source emits, as the measuring light, light having light intensity that is changed due to the change in the optical characteristics of the object detection member.

3. The light intensity detector according to claim 1, wherein the first light source and the second light source are light sources emitting lights on the basis of same principle, and
the first light source and the second light source are subjected to lighting control such that accumulated turned-on times of both the light sources are equal to each other.

4. The light intensity detector according to claim 1, wherein the second light source is arranged close to the first light source.

5. The light intensity detector according to claim 1, wherein the first light source and the second light source are implemented with a monolithic semiconductor laser.

6. The light intensity detector according to claim 1, wherein the first light detection unit and the second light detection unit are constituted as a single light detection unit, and
the first light source and the second light source are subjected to lighting control at different timings.

7. The light intensity detector according to claim 1, further comprising a pseudo object detection member having optical characteristics that are same as the optical characteristics of the object detection member under environment in which the object is not present,
wherein the light intensity of the reference light is detected by the light detection unit after being affected by the optical characteristics of the pseudo object detection member.

8. A detection method comprising:
a measuring light emitting step of emitting, from a first light source, measuring light used to measure the concentration of the object;
a measuring light detecting step of detecting, by a first light detection unit, light intensity of the measuring light that has been applied to an object detection member having optical characteristics changeable depending on a concentration of an object, the light intensity of the measuring light being changed due to a change in the optical characteristics of the object detection member;
a reference light emitting step of emitting, from a second light source arranged under same environment as that of the first light source, reference light used to correct the light intensity of the measuring light, which has been detected by the first light detection unit; and
a reference light detecting step of detecting, by a second light detection unit, light intensity of the reference light without being affected by the change in the optical characteristics of the object detection member.

* * * * *